United States Patent [19]

Bryson

[11] 4,213,923
[45] Jul. 22, 1980

[54] ENVIRONMENTAL CONTROL UNIT AND METHOD

[75] Inventor: John D. Bryson, Milwaukee, Wis.

[73] Assignee: Will Ross, Inc., Milwaukee, Wis.

[21] Appl. No.: 31,662

[22] Filed: Apr. 19, 1979

[51] Int. Cl.$^2$ ............................................... B01F 3/04
[52] U.S. Cl. .............................. 261/120; 210/242 A;
261/119 R; 261/DIG. 17
[58] Field of Search ................... 261/119 R, 120, 124,
261/125, DIG. 17, DIG. 65; 48/195; 210/242 A

[56] References Cited

U.S. PATENT DOCUMENTS

| 557,086 | 3/1896 | Schroeder | 261/120 X |
|---|---|---|---|
| 1,411,950 | 4/1922 | Wyatt | 261/120 |
| 2,074,367 | 3/1937 | Cordes | 261/120 |
| 2,171,893 | 9/1939 | Robinson | 261/120 |
| 2,203,362 | 6/1940 | Putnam | 261/DIG. 17 |
| 3,436,162 | 4/1969 | Nohl et al. | 261/120 X |
| 3,664,647 | 5/1972 | Snow et al. | 261/120 X |
| 4,029,581 | 6/1977 | Clough, Jr. et al. | 261/124 X |

*Primary Examiner*—Richard L. Chiesa
*Attorney, Agent, or Firm*—John A. Dhuey; James R. Henes

[57] ABSTRACT

A central source of odor neutralizing vapor fed into a floating or partially suspended distribution network is used to control odors from the surface of odiferous ponds having large surface areas.

7 Claims, 6 Drawing Figures

ENVIRONMENTAL CONTROL UNIT AND METHOD

BACKGROUND OF THE INVENTION

Sewerage treatment facilities which improve the quality of fluid waste often have odor problems associated with them. A common source of odors at such facilities are sludge ponds which retain fluid waste for extended periods of time to permit waste material to settle and be biodegraded into harmless sludge. Such ponds can be and most often are extended over very large areas in order to accomodate the large fluid volume generated by sewerage treatment facilities and the necessary residence time of fluid in the pond in order for settling and biodegradation to take place. Typically, such treatment or settling ponds can have surface areas ranging from hundreds of square feet to acres.

Prior attempts to control odors from such treatment facilities have generally been limited to treatment of the air mass surrounding the periphery of the pond with a masking or substitute odor such as provided by perfume or the like. Typically, an extended pipe has been placed near the periphery of the pond and masking vapor has been dispensed into the atmosphere through openings in the pipe wall. When dispensing pipes are placed only on the periphery of the pond, wind direction can be a substantial factor in the effectiveness of such peripheral units since the wind may serve to dispense the ordor in a pattern not reached by the limited perimeter odor abatement gas coverage.

Alternatively, treatment has been conducted simply by dispensing odorant into the air mass near the pond with reliance on the wind to disperse the odorant and thereby mask the effect of the odor causing material. Such systems are highly inefficient because of the large amount of odorant usually required and problems of dispersion into the air mass containing the odor causing material.

SUMMARY OF THE INVENTION

The invention provides a dispensing unit system and method for the controlled distribution of odor neutralizing vapor or odorant into the atmosphere over the fluid surface area of a pond. More particularly, the invention provides an environmental control unit for dispensing odor neutralizing vapor or odorant vapor over a fluid surface having means for dispensing the vapor which are supported by the buoyant forces exerted by the fluid and which are supplied with a neutralizing or odorizing vapor.

In one embodiment of the invention, the dispensing means comprises a plurality of plastic envelopes on conduits which are filled with a mixture of air and neutralizing vapor and which are floated on the surface of the fluid in the pond. The envelopes or conduits are supported, in a preferred embodiment, only by the buoyant forces exerted by the fluid. Each of the conduits or envelopes can be in fluid communication with an individual source of vapor, although it has been found preferable to attach a plurality of envelopes or conduits to a central source of vapor. Thus, for example, a single feeder conduit or several feeder conduits, either rigid or flexible, are placed along one or more sides of the pond retaining the fluid and the distribution envelopes or conduits are connected to each of the feeder conduits along its length.

Depending on the shape of the fluid retention pond, alternative distribution patterns for the dispensing envelopes or conduits can be utilized. For example, rectangular ponds may be treated by using a feeder conduit along one side thereof or several feeder conduits along the side with dispensing envelopes or conduits extending perpendicular to the feeder conduits and extending across the surface of the pond in parallel arrangement. For circular or oval retention ponds, it is desirable to arrange the feeder conduit around the circumference of the pond with the dispensing envelopes or conduits being arranged on the radii of the pond. For irregularly shaped retention ponds, the same principles can be used although envelopes and conduits of varying lengths are used.

Although the present invention is directed in its preferred embodiment to dispensing means which are totally supported by the buoyant forces of the fluid in the retention pond, it may be desirable to partially support the envelopes or pipes within the pond in certain circumstances, although such support usually would not be necessary. It is apparent that the support requirements would be reduced greatly by the upward buoyant forces exerted by the fluid even in the partially supported configuration.

Particularly in the case when the dispensing envelopes are non-rigid, it is desirable to anchor the ends of the conduits along the peripheral edge of the retention pond. In most instances, such anchoring does not support the dispensing envelopes or conduits but only serves to hold the dispensing means in its preferred distribution configuration, i.e. parallel, radial or the like.

Figure 1:
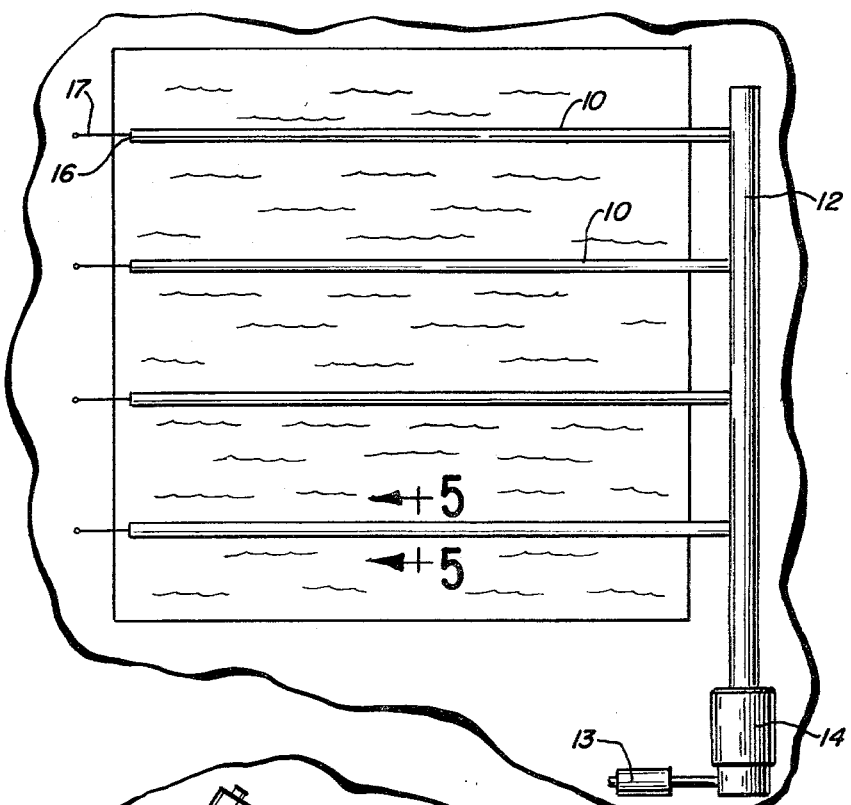
FIG. 1 is a top plan view of a typical rectangular retention pond illustrating various features of the invention.

Before explaining at least several embodiments of the invention in detail, it is to be understood that the invention is not limited in its application to the details of construction and arrangement of the components set forth in the following description or illustrated in the drawings. The invention is capable of other embodiments and of being practiced and carried out in various ways. Also, it is to be understood that the phraseology and terminology employed herein are for the purposes of description and should not be regarded as limiting.

DESCRIPTION OF THE PREFERRED EMBODIMENTS

Figure 2:
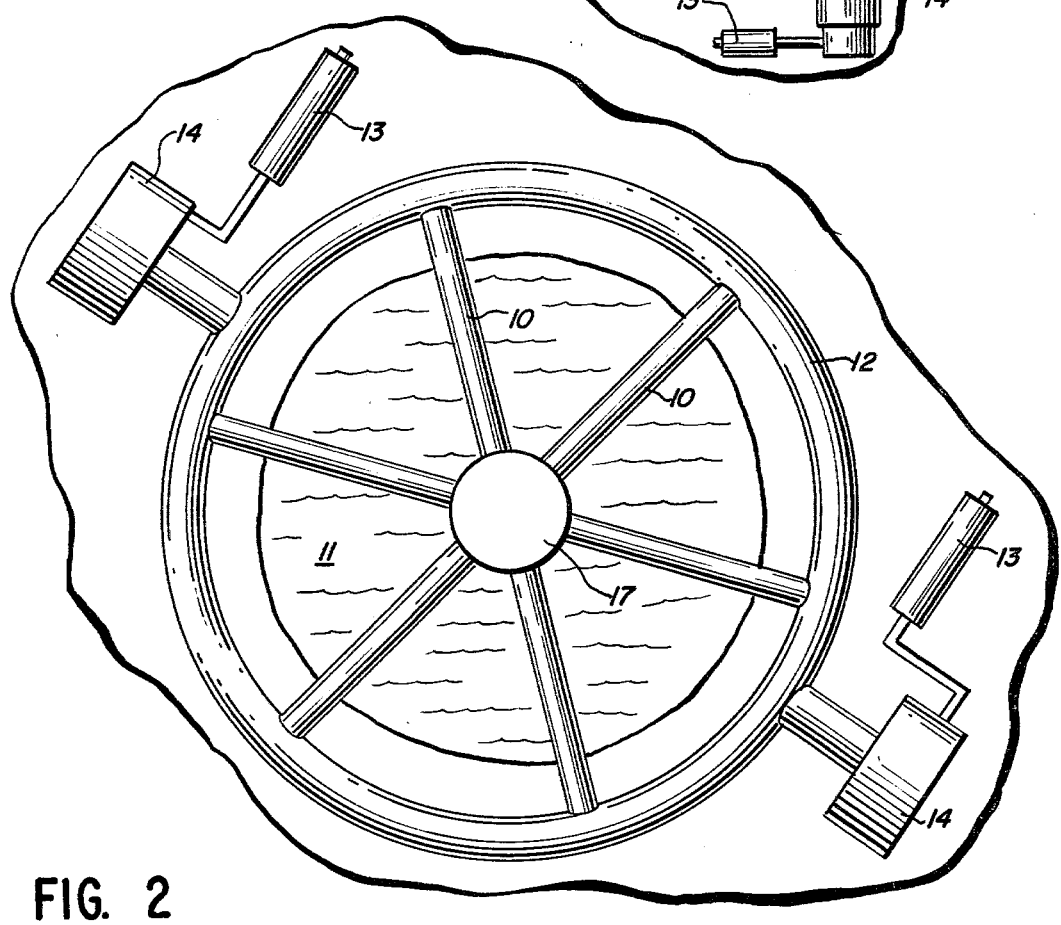
FIG. 2 is a top plan view of another embodiment of the invention for application to circular areas.
Figure 3:
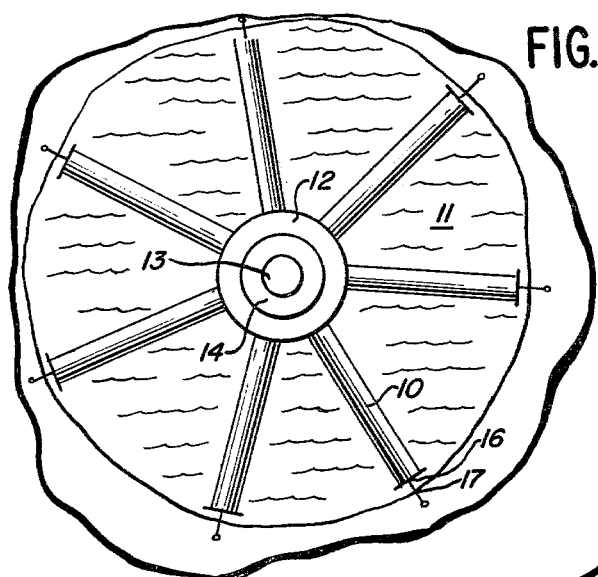
FIG. 3 is a top plan view of still another embodiment of the invention utilizing a central feeder system.
Figure 4:
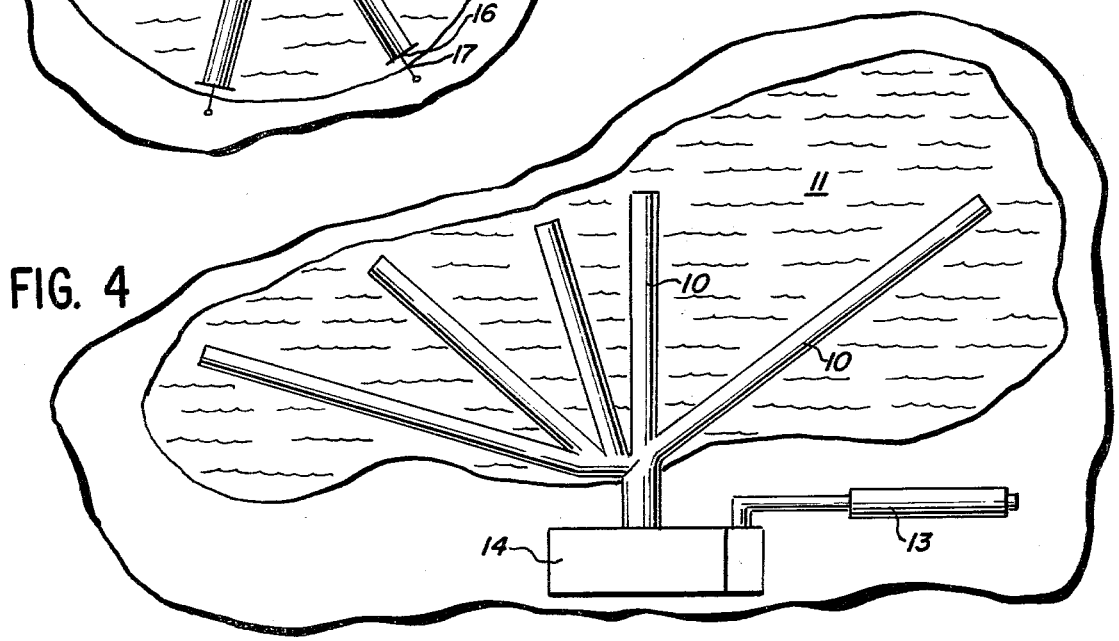
FIG. 4 is a top plan view of a variation of the invention as applied to irregular areas.

As illustrated in the drawings, the invention comprises conduits or envelopes 10 supported on the surface of a pond 11 by the buoyant forces exerted by the fluid. Polyethylene tubing has been found to be eminently suitable as a material for conduits or envelopes 10. Other materials which permit support by the buoyant forces of the fluid are suitable as well. The conduits 10 are attached to and in fluid communication with a supply pipe 12 through which air and neutralizing vapor or odorant is passed by means such as a blower 14. The neutralizing vapor is drawn into the blower inlet and mixed with inlet air, and the air-vapor mixture is fed through conduits 10. Conduits 10 are attached to supply pipe 12 at one end by ordinary means such as connecting flanges or the like and preferably anchored at their other end 16 by anchoring means 17. Typically, anchoring means 17 can be a wire extending from the area adjacent the pond to the end of conduit 10. The anchoring means 17 does not serve to support conduits 10 to any great extent but instead prevents the conduits 10 from moving out of their planned distribution pattern. Those distribution patterns are shown particularly in FIG. 1 which is a parallel pattern, FIGS. 2 and 3 which are radial patterns and FIG. 4 which is a pattern for an irregular area. Other patterns may be used as well depending on the particular requirements of various situations and will be apparent to those skilled in the art.

Figure 5:
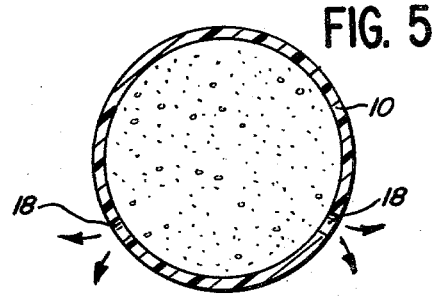
FIG. 5 is a cross-section of one conduit of this invention.

In FIG. 5 is illustrated a preferred arrangement of the orifice holes 18 in conduit 10. The holes 18 are placed below the median plane of conduit 10 and above the fluid surface and serve to direct the neutralizing vapor downwardly onto the surface of the pond. In particular instances, it may be desirable to employ a nozzle (not shown) within orifice holes 18 to control the flow of neutralizing vapor therethrough.

Figure 6:
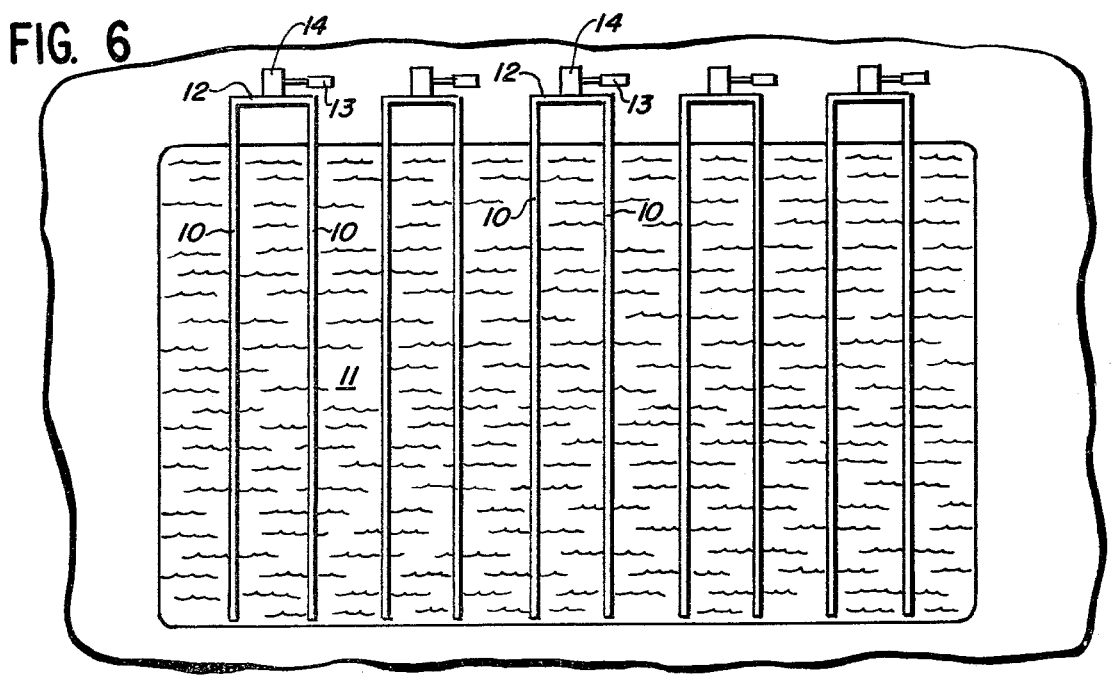
FIG. 6 is a top plan view of a rectangular retention pond using several feeder conduits.

FIG. 6 illustrates the embodiment wherein a plurality of feeder or supply pipes 12 are utilized. The remainder of the apparatus remains as hereinbefore described.

Required air flow rates, concentration of neutralizing vapor feed rates and particular design of the distribution system can be varied to the particular treatment situation at hand. The following example is given for illustration purposes only and is not intended to limit the invention.

EXAMPLE

On a retention pond 400 feet by 600 feet a supply of air is provided every 120 feet by 5, 1 horsepower, 30 inch, 10,000 CFM fan blowers which are each connected to two 30 inch conduits to provide a parallel arrangement of conduit 120 feet apart. An odor control unit it supply neutralizing vapor is connected to the air supply serving two of the conduits at one time. As air is drawn into the fan-blowers, the neutralizing vapor is drawn from the odor control unit and passes into the air stream. One hundred and thirty-three pairs of holes on three foot centers and of a diameter of about 2.4 inches are provided in each conduit. The gauge pressure at each housing is "2–3" of water and the differential head across the orifices is 0.2 inches of water and a mean velocity in the conduits of 18 feet/sec. is provided.

What is claimed is:

1. An environmental control unit for dispensing odor neutralizing vapor over a liquid surface comprising:
   a plurality of conduits for dispensing odor neutralizing vapor over the liquid surface, each of said conduits being partially submerged and sufficiently buoyant to be supported on the surface of the liquid at least partially by buoyant forces exerted by the liquid and having vapor dispensing outlets thereon located above the surface of the liquid and directing the vapor downwardly over the liquid surface; and
   a central source of the vapor in fluid communication with said conduits.

2. A unit as in claim 1 further comprising anchoring means at one end of each of said conduits.

3. A unit as in claim 1 wherein said conduits have orifices below the median plane of said conduits for directing the vapor downwardly on the surface of the liquid.

4. A unit as in claim 1 wherein said conduits are arranged parallel to each other on the surface of the liquid and are fed from a common manifold.

5. A unit as in claim 1 wherein said conduits are inflatable envelopes.

6. A unit as in claim 1 wherein each of said conduits is generally cylindrical.

7. A unit as in claim 1 wherein each of said dispensing outlets on each of said conduits includes a nozzle in fluid communication with the inside of said conduit.

* * * * *